United States Patent [19]

Adolph et al.

[11] Patent Number: 4,745,208
[45] Date of Patent: May 17, 1988

[54] 2,2,2-TRINITROETHYL 2-NITROXYETHYL ETHER AND A METHOD OF PREPARATION

[75] Inventors: Horst G. Adolph, Silver Spring; Kyung E. Kim, Potomac, both of Md.

[73] Assignee: The United States of America as represented by the Secretary of the Navy, Washington, D.C.

[21] Appl. No.: 43,267

[22] Filed: Apr. 27, 1987

[51] Int. Cl.$^4$ .............................................. C07C 77/02
[52] U.S. Cl. ................... 558/483; 558/480; 568/589; 149/88
[58] Field of Search ............ 558/480, 483; 149/88; 568/583, 589

[56] References Cited

U.S. PATENT DOCUMENTS 3,079,425  2/1963  Mortimer ........................... 558/483

Primary Examiner—Edward A. Miller
Assistant Examiner—Susan Wolffe
Attorney, Agent, or Firm—Kenneth E. Walden; Roger D. Johnson

[57] ABSTRACT

2,2,2-trinitroethyl 2-nitroxyethyl ether (TNEN), $C(NO_2)_3CH_2OCH_2CH_2ONO_2$, which is prepared by the following reaction sequence:

$$C(NO_2)_3^-K^+ + ClCH_2OCH_2CH_2BR \rightarrow C(NO_2)_3CH_2OCH_2CH_2Br$$
$$C(NO_2)_3CH_2OCH_2CH_2Br + AgNO_3 \rightarrow C(NO_2)_3CH_2OCH_2CH_2ONO_2.$$

2,2,2-trinitroethyl 2-nitroxyethyl ether is useful an an energetic plasticizer, for example in LOVA gun propellants.

3 Claims, No Drawings

2,2,2-TRINITROETHYL 2-NITROXYETHYL ETHER AND A METHOD OF PREPARATION

BACKGROUND OF THE INVENTION

This invention relates to organic ethers and more particularly to energetic polynitro organic ethers.

Plasticizers which are commonly used in gun propellants and other energetic compositions are nitroglycerin (NG), butanetriol trinitrate (BTTN), metriol trinitrate (METN), and diethylene glycol dinitrate (DEGN). Nitroglycerin and butanetriol trinitrate having relatively low thermal stabilities due to the presence of secondary hydroxy groups. Metriol trinitrate and diethylene glycol dinitrate have relatively low energies. Nitroglycerin and diethylene glycol dinitrate also have the disadvantage of high vapor pressures.

It would be desirable to provide a new energetic plasticizer having a high energy density, good thermal stability, good plasticizing ability, and a low vapor pressure.

SUMMARY OF THE INVENTION

Accordingly, an object of this invention is to provide a new energetic plasticizer for propellants and explosives.

Another object of this invention is to provide an energetic plasticizer having a high energy content.

A further object of this invention is to provide an energetic plasticizer having a good thermal stability.

Still another object of this invention is to provide an energetic plasticizer having a low vapor pressure.

A still further object of this invention is to provide an energetic plasticizer having a good plasticizing ability for polymers commonly used in propellant and explosive composites.

These and other objects of this invention are achieved by providing:

2,2,2-trinitroethyl 2-nitroxyethyl ether, $C(NO_2)_3CH_2OCH_2CH_2ONO_2$, which is prepared by (1) reacting one mole of potassium nitroform with one mole of chloromethyl 2-bromoethyl ether to produce 2,2,2-trinitroethyl 2-bromoethyl ether;

(2) reacting the 2,2,2-trinitroethyl 2-bromoethyl ether with silver nitrate to form 2,2,2-trinitroethyl 2-nitroxyethyl ether; and (3) isolating the desired product 2,2,2-trinitroethyl 2-nitroxyethyl ether.

2,2,2-trinitroethyl 2-nitroxyethyl ether is useful as an energetic plasticizer in propellant and explosive compositions such as LOVA gun propellants.

DETAILED DESCRIPTION OF THE PREFERRED EMBODIMENT 2,2,2-trinitroethyl 2-nitroxyethyl ether (TNEN) is a new energetic plasticizer. The energy content of TNEN is between that of nitroglycerin (NG) and butanetriol trinitrate (BTTN). The melting point of TNEN is lower than that of nitroglycerin (11° C. vs. 14° C.) and TNEN is less volatile and thus less toxic than nitroglycerin. TNEN is far more thermally stable than either nitroglycerin or butanetriol trinitrate, with TNEN producing only 1.5 ml/g of gas in 48 hours at 100° C. Trinitroethyl nitroxyethyl ether (TNEN) is a plasticizer for cellulose acetate butyrate (CAB), nitrocellulose (NC), polyethylene glycol (PEG), polycaprolactone (PCP) and other polymers. The plasticized polymer is usually prepared from a solution of the plasticizer and polymer in a common volatile solvent, such as ethyl acetate, by removal of the solvent. For example, rubbery gum stocks have been prepared from ethyl acetate solutions of (1) TNEN and nitrocellulose and (2) TNEN and cellulose acetate butyrate by evaporating off the solvent.

2,2,2-trinitroethyl 2-nitroxyethyl ether (TNEN) is prepared by the reaction of potassium nitroform with chloromethyl 2 2-bromoethyl ether to form 2,2,2-trinitroethyl 2-bromoethyl ether which is then reacted with silver nitrate to form the desired product TNEN as shown in the following reaction scheme:

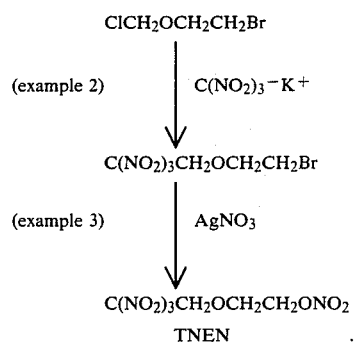

Example 1 shows a method of preparing the starting material chloromethyl 2-bromoethyl ether. Example 2 illustrates suitable conditions for reacting potassium nitroform with chloromethyl 2-bromoethyl ether to produce the intermediate product 2,2,2-trinitroethyl 2-bromoethyl ether. Finally, example 3 illustrates suitable conditions for reacting the 2,2,2-trinitroethyl 2-bromoethyl ether with silver nitrate to produce the final product 2,2,2-trinitroethyl 2-nitroxyethyl ether.

The general nature of the invention having been set forth, the following examples are presented as specific illustrations thereof. It will be understood that the invention is not limited to these specific examples but is susceptible to various modifications that will be recognized by one of ordinary skill in the art.

EXAMPLE 1 chloromethyl 2-bromoethyl ether

In a 3-neck flask under nitrogen, 41.2 g of 2-bromoethanol and 10 g of trioxane were dissolved in 250 ml of dry dichloromethane. Then 44 g of $AlCl_3$ were added rapidly with vigorous stirring, and stirring was continued for 4 hours. The reaction mixture was poured over crushed ice, the product was extracted into dichloromethane, and this solution was rapidly washed twice with ice-cold water. After drying ($MgSO_4$) and filtering, the dichloromethane was distilled off and the chloromethyl 2-bromoethyl ether was fractionated: b.p. 84°–9° C. (20 torr), yield 22.8 g (39.7%).

EXAMPLE 2

2,2,2-trinitroethyl 2-bromoethyl ether

In a 3-neck flask under a nitrogen atmosphere 24.36 g of potassium nitroform was stirred in 60 ml of anhydrous acetone. 21.13 of the chloromethyl 2-bromoethyl ether prepared in example 1 was then added dropwise with stirring. Stirring was continued for 48 hours. The reaction mixture was poured into water and stirred vigorously for 1–2 hours. The product was extracted with dichloromethane, the extract was washed with water and 5% aqueous NaHCO$_3$ solution, dried over MgSO$_4$, filtered and freed form solvent under vacuum. Obtained was 21.81 g of crude trinitroethyl bromoethyl ether which was purified on silica gel (Kieselgel 60, 70–230 mesh) using a 1:1 mixture of hexane and dichloromethane as eluent. The weight of the pure product was 10.7 g (30%), MP 0.6°–2.2° C.

EXAMPLE 3

2,2,2-trinitroethyl 2-nitroxyethyl ether

In a 3-neck flask under a nitrogen atmosphere 7.05 g of silver nitrate was dissolved in 35 ml of anhydrous acetonitrile. With ice-cooling 10.5 g of trinitroethyl 2-bromoethyl ether was added dropwise and the reaction mixture was stirred at 45° C. for seven days. The mixture was filtered and the solid was washed thoroughly with dichloromethane. The filtrate was washed with water and 5% aqueous NaHCO$_3$ solution, dried (MgSO$_4$) and freed from solvent under vacuum. Obtained was 7.1 g of crude 2,2,2-trinitroethyl 2-nitroxyethyl ether which was purified on silica gel (Kieselgel 60, 70-230 mesh) using a 6:4 mixture of hexane-dichloromethane as eluent. 3.54 g (36.1%) of pure 2,2,2-trinitroethyl 2-nitroxyethyl was ether recovered, MP 10°–11° C., density 1.55 g/cm$^3$. Analysis—Calc'd for C$_4$H$_6$N$_4$O$_{10}$: C, 17.8%; N, 20.7%; H, 2.2%. Found: C, 17.71%; N, 19.65%; H, 2.14%.

$^1$H NMR (CDCl$_3$): δ4.08 (t, 2H), 4.72 (t, 2H) 4.88 (s 2H).

Obviously numerous modifications and variations of the present invention are possible in light of the above teachings. It is therefore to be understood that within the scope of the appended claims the invention may be practiced otherwise than as specifically described herein.

What is claimed is:

1. 2,2,2-trinitroethyl 2-nitroxyethyl ether, C(NO$_2$)$_3$CH$_2$OCH$_2$CH$_2$ONO$_2$.

2. 2,2,2-trinitroethyl 2-bromoethyl ether, C(NO$_2$)$_3$CH$_2$OCH$_2$CH$_2$Br.

3. A process for preparing 2,2,2-trinitroethyl 2-nitroxyethyl ether comprising the following steps in order:
    (1) reacting one mole of potassium nitroform with one mole of chloromethyl 2-bromoethyl ether to produce 2,2,2-trinitroethyl 2-bromoethyl ether;
    (2) reacting the 2,2,2-trinitroethyl 2-bromoethyl ether with silver nitrate to form 2,2,2-trinitroethyl 2-nitroxyethyl ether; and
    (3) isolating the product 2,2,2-trinitroethyl 2-nitroxyethyl ether.

* * * * *